United States Patent [19]
Schmitt et al.

[11] Patent Number: 4,745,232
[45] Date of Patent: May 17, 1988

[54] PROCESS FOR PREPARING 4,6-DINITRORESORCINOL

[75] Inventors: Robert J. Schmitt, Mountain View; David S. Ross; James F. Wolfe, both of Palo Alto, all of Calif.

[73] Assignee: SRI International, Menlo Park, Calif.

[21] Appl. No.: 1,243

[22] Filed: Jan. 7, 1987

[51] Int. Cl.$^4$ ............................................. C07C 79/28
[52] U.S. Cl. ..................................... 568/712; 568/711
[58] Field of Search ................. 568/710, 711; 868/712

[56] References Cited

U.S. PATENT DOCUMENTS

| | | | |
|---|---|---|---|
| 1,380,186 | 5/1921 | Brewster | 568/712 |
| 2,945,890 | 7/1960 | Allan | 260/622 |
| 3,694,513 | 9/1972 | Tobey et al. | 568/711 |
| 3,933,926 | 1/1976 | Salter et al. | 568/711 |

FOREIGN PATENT DOCUMENTS

| 573768 | 4/1959 | Canada | 568/711 |
|---|---|---|---|
| 1098932 | 6/1984 | U.S.S.R. | 568/711 |

OTHER PUBLICATIONS

Fitzpatrick et al., *J. Chem. Soc.* Perkin Trans. II: 927–932 (1984).

*Primary Examiner*—Warren B. Lone
*Attorney, Agent, or Firm*—Ciotti & Murashige, Irell & Manella

[57] ABSTRACT

A method of nitrating resorcinol which is selective for the production of the 4,6-dinitro resorcinal isomer. A resorcinol-based starting material is admixed with a nitrating solution from which substantially all nitrogen dioxide and nitrous has been removed. The nitrating solution contains white fuming nitric acid, a nitrosonium ion control agent such as urea, and, optionally, concentrated sulfuric acid. The 4,6-dinitroresorcinal isomer is provided in yields of about 65–85% with minimal production of undesirable side products.

18 Claims, No Drawings

PROCESS FOR PREPARING 4,6-DINITRORESORCINOL

This invention was made with government support under contract F49620-83-K-0036 awarded by the United States Air Force. The government has certain rights in this invention.

BACKGROUND OF THE INVENTION

1. Field of the Invention

This invention relates generally to methods of synthesizing nitrophenols, and more particularly relates to a method of selectively synthesizing 4,6-dinitro resorcinol.

2. Description of the Prior Art

Direct nitration of phenolic compounds is typically highly exothermic and difficult to control. Because nitrophenols are synthetically important compounds, however, their controlled preparation in high yield is desirable. Further, it is also desirable that the number and complexity of intermediate steps be kept to a minimum in order to reduce the time and cost involved in synthesis.

The present invention is directed to the nitration of resorcinol (1,3-dihydroxybenzene; Formula 1). In particular, this invention is directed to a method of selectively synthesizing the 4,6-dinitroresorcinol isomer (Formula 2), which compound is a useful intermediate in the preparation of poly[p-phenylenebenzobisoxazole] ("PBO") and related compounds. As is well known, PBO (Formula 3) is a high-strength, liquid crystalline material with many applications.

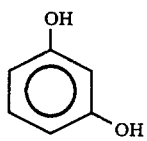

Formula 1

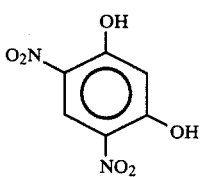

Formula 2

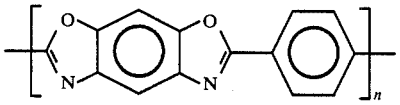

Formula 3

Several syntheses of nitrophenols and of nitroresorcinol monomers in particular have been proposed.

U.S. Pat. No. 1,380,186 to Brewster discloses a method of synthesizing picric acid (2,4,6-trinitrophenol) from phenol using a nitric acid based solution. Brewster, however, does not disclose a method that will preferentially produce either mono- or dinitro compounds in substantial quantities.

U.S. Pat. No. 2,945,890 to Allan shows a method of preparing 2,4-dinitroresorcinol using a sulfuric acid/nitric acid nitrating solution. Apparently, however, styphnic acid (2,4,6-trinitroresorcinol), an undesirable and explosive side product, is also produced in fairly substantial quantities.

U.S. Pat. No. 3,933,926 to Salter discloses an alternative method of preparing 2,4-dinitroresorcinol. Salter proposes nitrosation of resorcinol followed by oxidation of the nitroso groups to nitro substituents. Again, styphnic acid is produced as a side product.

Neither of these two latter processes have been modified successfully to produce 4,6-dinitroresorcinol, the isomer to which the present method is directed. One method which has been used to synthesize 4,6-dinitro resorcinol is admixture of resorcinol diacetate with a 1:1 solution of 70% $HNO_3$ and 90% red fuming $HNO_3$ ("red" here indicating the presence of $NO_2$ in solution). This process has been described in G. C. Berry et al., Air Force Technical Report AFML-TR-79-4115 (August 1979). This procedure, however, gives both a low yield of 4,6-dinitroresorcinol—less than 45%—and simultaneous production of styphnic acid in yields ranging from 30% to 60%.

For additional material on nitration of aromatic compounds, reference may be had to K. Schofield, *Aromatic Nitration* (Cambridge: Cambridge University Press, 1980).

Thus, there is a need in the art for a method of preparing 4,6-dinitroresorcinol in a high yield with a minimum of undesirable side products.

SUMMARY OF THE INVENTION

Accordingly, it is an object of the present invention to provide a controlled method of synthesizing 4,6-dinitroresorcinol in high yield while minimizing the production of undesirable side products such as styphnic acid.

It is another object of the present invention to provide a synthesis of 4,6-dinitroresorcinol, which synthesis substantially reduces styphnic acid production by removing $NO_2$ and nitrous acid from solution.

It is a further object of the present invention to provide a method of synthesizing 4,6-dinitro resorcinol using inexpensive and readily available reagents.

It is still a further object of the present invention to provide a method of synthesizing 4,6-dinitroresorcinol in high yield while minimizing the number of synthetic steps involved.

Additional objects, advantages and novel features of the invention will be set forth in part in the description which follows, and in part will become apparent to those skilled in the art on examination of the following, or may be learned by practice of the invention.

In one aspect of the present invention, a method comprises a temperature-controlled procedure whereby 4,6-dinitroresorcinol is selectively synthesized in white fuming nitric acid from a resorcinol-based starting material. The reaction is carried out in the presence of a nitrosonium ion control agent in order to minimize nitrosonium-catalyzed side reactions. Styphnic acid production is thus substantially reduced, and 4,6-dinitroresorcinol is typically prepared in about an 80% yield.

In another aspect of the invention, 4,6-dinitroresorcinol is synthesized from a resorcinol-based starting material according to a method that is substantially similar to that outlined above; however, sulfuric acid is the primary reaction medium. This synthetic version provides a rapid reaction using inexpensive reagents. Yields of 4,6-dinitroresorcinol in this procedure are on the order of at least about 65%.

DETAILED DESCRIPTION OF THE INVENTION

The present invention provides a method of synthesizing 4,6-dinitroresorcinol monomers, precursors to the high-strength, liquid crystalline polymer PBO, in very high yield with a minimum of styphnic acid or 2,4-dinitroresorcinol production. This is in contrast to the more complex prior art methods in which, as noted, 4,6-dinitroresorcinol was produced in a much lower yield, often along with substantial quantities of undesirable side products.

In one embodiment of the invention, a resorcinol-based starting material is provided having the structure given by Formula 4

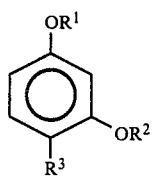

Formula 4 where $R^1$ and $R^2$ are independently selected from the group consisting of hydrogen and a protecting moiety given by

where R is hydrogen or a lower alkyl substituent (about 1–3 carbon atoms), and $R^3$ is either hydrogen, a nitro, or a nitroso substituent, with the proviso that $R^1$, $R^2$ and $R^3$ are not all hydrogen. As will be understood by those of ordinary skill in the art, the available hydrogen atoms at the 2- and 5-positions of the aromatic ring may be substituted with halogen atoms and lower alkyl and alkoxy groups which do not substantially adversely affect the nitration reaction. The reaction of the present invention as described herein encompasses nitration of reactants consistent with this understanding.

Suitable starting materials are thus resorcinol compounds which have been deactivated so as to be less reactive to electrophilic substitution. Unsubstituted resorcinol, for example, is not a preferred starting material. Preferred starting materials do include, inter alia, resorcinol monoacetate, resorcinol diacetate, 4-nitroresorcinol, 4-nitroresorcinol monoacetate, 4-nitroresorcinol diacetate, 4-nitrosoresorcinol, 4-nitrosoresorcinol monoacetate and 4-nitroresorcinol diacetate.

A reaction medium for nitration of the starting material is prepared as follows. Oxygen or any inert gas is bubbled through concentrated nitric acid having a concentration between about 70 wt.% and about 90 wt.%, preferably about 70 wt.%, until the acid is colorless. This "white" fuming acid which has been so purged is substantially free of $NO_2$ and nitrous acid, as opposed to the "red" acid from which it is derived. Since $NO_2$ and nitrous acid contribute to the formation of the nitrosonium ion $NO^+$, which in turn results in nitration at the 2-position of the starting material (to form, for example, styphnic acid and 2,4-dinitroresorcinol), elimination of $NO_2$ from the reaction mixture increases the purity of the 4,6-dinitroresorcinol product ultimately prepared.

Prior to addition of the resorcinol-based starting material to the reaction medium, a nitrosonium ion control agent is added to the purged nitric acid in order to further ensure that undesirable nitrosonium ion-catalyzed side reactions are prevented. Suitable nitrosonium ion control agents are those which react with $NO_2$ or nitrous acid so as to prevent conversion of these compounds to $NO^+$. Preferred nitrosonium ion control agents include compounds having a primary amine group. Examples of exemplary nitrosonium ion control agents are urea, hydrazine, sulfamic acid, 4-nitro aniline, 2,4-dinitroaniline, hydroxylamine, sulfanilic acid, hydrazoic acid and sulfanilamide. The quantity of nitrosonium control agent added is preferably between about 0.01 wt.% and about 10.0 wt.%.

After addition of the control agent to the nitric acid, the solution is cooled to a temperature of between about $-20°$ C. and about $25°$ C., preferably between about $-10°$ C. and $0°$ C. While a preferred reaction temperature is approximately $0°$ C., a faster reaction may be obtained, if desired, with higher temperatures.

The selected resorcinol compound is then gradually added, while stirring, to the cooled reaction medium. Preferred final concentration of starting material is between about 0.1 and 4 g to 10 ml final solution, more preferably about 0.5 g to 10 ml final solution. The solution is stirred for at least about an hour, after which time additional concentrated white fuming nitric acid preferably having a concentration of at least about 80 wt.%, more preferably about 90 wt.%, or $N_2O_5$ solid, is added to the reaction mixture until an overall nitric acid concentration of about 80 wt.% is reached.

After this latter step, the reaction mixture is stirred until precipitation of 4,6-dinitroresorcinol, a yellowish-gold solid, appears complete. Typically at least about 2 hours, preferably about 5 hours, should be allowed for reaction completion. The precipitated 4,6-dinitroresorcinol is isolated by filtration. In order to maximize recovery, the remaining solution is poured onto ice and filtered again to remove any additional precipitate.

The isolated 4,6-dinitroresorcinol is then purified, preferably by recrystallization in ethyl acetate or in any other suitable solvent.

The initial concentration of nitric acid can be varied from about 70 wt.% to about 90 wt.%, depending on the temperature and contact time for the reaction. The resorcinol starting material can be added directly to solutions of 80 wt.% nitric acid or less. For more concentrated acids (for example, where a faster reaction is desired), the resorcinol should first be dissolved in 70 to 80 wt.% nitric acid, and more concentrated nitric acid may then be added. With initial nitric acid concentrations of greater than about 80 wt.%, contact time should be kept short, i.e., less than about 1 hour, in order to minimize nitration to undesirable side products.

The foregoing procedure provides 4,6-dinitroresorcinol in about an 80% yield, with the bulk of the remainder being 4-nitroresorcinol (10–15%). Any 4-nitroresorcinol so obtained may be recycled through the synthetic sequence in order to provide additional 4,6-dinitroresorcinol.

In a second embodiment of the invention, 4,6-dinitroresorcinol is synthesized in a reaction medium that is primarily sulfuric acid. The basic reaction steps of this procedure are substantially identical to those outlined above. However, this process, which employs sulfuric rather than nitric acid, is generaly preferred for reasons of safety and economy.

In this embodiment, a resorcinol compound as defined by Formula 4 is added to a nitrating solution maintained at a temperature within the range set forth above. The nitrating solution contains both nitric acid and a nitrosonium ion control agent as above. In this synthetic version, however, the nitrating solution, which is primarily sulfuric acid, is prepared as follows. Two to ten equivalents of white fuming nitric acid (i.e. nitric acid which has been purified as already described) or sodium or potassium nitrate or $N_2O_5$ are added to a sulfuric acid solution having an initial concentration of between about 60 wt.% and 96 wt.%, preferably between about 75 wt.% and about 83 wt.%. The solution is then cooled to the desired temperature, between about $-10°$ C. and 25° C., and a suitable amount of a nitrosonium ion control agent is added. The resorcinol compound is then added as well, and the reaction is allowed to proceed as above.

The 4,6-dinitroresorcinol compound prepared by this latter method is generally produced in at least a 75% yield; as noted, however, lower temperatures will generally provide a higher yield of the compound.

While the invention has been described in conjunction with the preferred specific embodiment thereof, it is to be understood that the foregoing description as well as the examples which follow are intended to illustrate and not limit the scope of the invention, which is defined by the appended claims. Other aspects, advantages and modifications within the scope of the invention will be apparent to those skilled in the art to which the invention pertains.

EXAMPLE 1

A nitric acid solution was used to prepare 4,6-dinitroresorcinol from resorcinol as follows. 1000 ml of 70 wt.% nitric acid (Mallinckrodt) was purified by passing oxygen through the acid until the red hue indicating the presence of nitrogen dioxide was no longer present. Urea (Mallinckrodt, 80 g) was added as a nitrosonium ion control agent, and the mixture was cooled to 0° C. Resorcinol diacetate (Mallinckrodt, 194 g) was slowly added, over a period of about 30 minutes, to the nitric acid solution with rapid stirring. After addition of resorcinol diacetate, the reaction mixture was stirred for one hour, after which time 90 wt.% white fuming nitric acid (again, made by bubbling oxygen through 90% red fuming nitric acid) was slowly added until an 80 wt.% concentration of nitric acid was reached at a total reaction volume about 2000 ml. During the course of the reaction, a yellowish-gold precipitate was observed to form. This precipitate was isolated by filtration, and the remaining solution was poured onto ice and filtered again. The product was characterized as 4,6-dinitroresorcinol by HPLC on a C18 Reverse Phase Column using an eluting solution containing acetonitrile, methanol, water, and 1% acetic acid (HPLC peaks: ~5.58 min., styphnic acid: ~12 min., 4-nitroresorcinol and 2,4-dinitroresorcinol: ~12.6 min., 4,6-dinitroresorcinol). Approximate yield after purification was about 65%.

EXAMPLE 2

An $H_2SO_4$-based nitrating solution was used to prepare 4,6-dinitroresorcinol as follows. 2.2 equivalents of 90 wt.% white fuming nitric acid (purified with oxygen to remove $NO_2$) were added to 60 ml. sulfuric acid (Baker) having a concentration of 80 wt.%. The acid mixture was cooled to a temperature of about 0° C., and 0.1 g. urea was added as a nitrosonium ion control agent. Five g. of resorcinol diacetate was then slowly added to the reaction mixture with rapid stirring. The reaction was stirred for an additional 3 hours, and the 4,6-dinitroresorcinol precipitate was isolated, purified and characterized as in Example 1. Approximate yield after purification was 75%.

EXAMPLE 3

The procedure of Example 2 was essentially repeated at about 10° C. with varying sulfuric acid concentrations so that the yield of the 4,6-dinitro resorcinol product could be optimized. The initial quantity of white fuming nitric acid (90 wt.%) was approximately 2.5 equivalents, i.e. relative to the resorcinol diacetate starting material. Relsults are set forth in Table 1:

TABLE 1

| $H_2SO_4$ conc., wt. % | Yield 4,6-dinitroresorcinol |
|---|---|
| 60.0 | 13.5% |
| 70.0 | 42.0% |
| 75.0 | 49.0% |
| 77.5 | 50.0% |
| 78.5 | 55.0% |
| 79.5 | 54.0% |
| 80.0 | 55.0% |
| 80.5 | 54.5% |
| 82.5 | 54.5% |
| 85.0 | 41.0% |
| 95.5 | 18.5% |

It may be concluded from these preliminary studies summarized in Table 1 that the optimum sulfuric acid concentration is at about 80 wt.% for a nitration with 2.5 equivalents $HNO_3$. It should be noted that higher yields, as in Example 2, were obtained at the lower temperatures used in the experimental work summarized therein.

We claim:

1. A process for preparing 4,6-dinitroresorcinol which minimizes side reactions catalyzed by the nitrosonium ion, comprising the steps of:

providing a resorcinol-based starting material having the structure

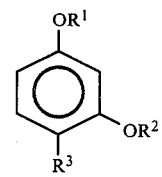

wherein $R^1$ and $R^2$ are independently selected from the group consisting of hydrogen and —C—R, R is hydrogen or lower alkyl, and $R^3$ is selected from the group consisting of hydrogen, nitro and nitroso, with the proviso that $R^1$, $R^2$ and $R^3$ are not all hydrogen;

purging a reaction medium containing nitric acid with an inert gas so as to remove substantially all $NO_2$ and nitrous acid therefrom;

adding to the reaction medium an amount of a nitrosonium ion control agent effective to minimize nitrosonium ion-catalyzed side reactions;

cooling the reaction medium to a temperature of between about $-20°$ C. and about 25° C.;

adding the resorcinol-based starting material to the cooled reaction medium; and allowing the starting material to react with the nitric acid while maintaining the temperature between about −20° C. and about 25° C. for a period of time selected so as to minimize styphnic acid production while sufficient to produce substantially complete precipitation of 4,6-dinitroresorcinol.

2. The process of claim 1, wherein the reaction medium is concentrated nitric acid.

3. The process of claim 2, wherein the temperature of the solution is maintained between about −10° C. and about 0° C.

4. The process of claim 2, wherein the resorcinol compound is selected from the group consisting of resorcinol monoacetate, resorcinol diacetate, 4-nitroresorcinol, 4-nitroresorcinol monoacetate and 4-nitroresorcinol diacetate.

5. The process of claim 2, wherein the nitrosonium ion control agent is a compound containing a primary amine group.

6. The process of claim 6, wherein the nitrosonium ion control agent is selected from the group consisting of urea, hydrazine, sulfamic acid, 4-nitroaniline, 2,4-dinitroaniline, hydroxylamine, sulfanilic acid, hydrazoic acid and sulfanilamide.

7. The process of claim 2, wherein the concentrated nitric acid is initially present at a concentration of between about 70 wt.% and about 90 wt.%.

8. The process of claim 7, wherein the concentrated nitric acid is initially present at a concentration of approximately 70 wt.%.

9. The process of claim 2, wherein after the addition of the starting material to the reaction medium, additional nitric acid is added to the reaction medium in an amount sufficient to bring the overall nitric acid concentration of the solution to at least about 80 wt.%.

10. The process of claim 9, wherein the additional nitric acid has a concentration of approximately 90 wt.%.

11. The process of claim 1, wherein the reaction medium is concentrated sulfuric acid.

12. The process of claim 11, wherein the sulfuric acid has an initial concentration of between about 60 wt.% and about 96 wt.%.

13. The process of claim 12, wherein the initial sulfuric acid concentration is between about 75 wt.% and 83 wt.%.

14. The process of claim 11, wherein the temperature of the solution is maintained between about −10° C. and about 0° C.

15. The process of claim 11, wherein the resorcinol compound is selected from the group consisting of resorcinol monoacetate, resorcinol diacetate, 4-nitroresorcinol, 4-nitroresorcinol monoacetate and 4-nitroresorcinol diacetate.

16. The process of claim 11, wherein the nitrosonium ion control agent is a compound containing a primary amine group.

17. The process of claim 16, wherein the nitrosonium ion control agent is selected from the group consisting of urea, hydrazine, sulfamic acid, 4-nitroaniline, 2,4-dinitroaniline, hydroxylamine, sulfanilic acid, hydrazoic acid and sulfanilamide.

18. The process of claim 11, wherein the reaction medium additionally includes a nitrating agent selected from the group consisting of sodium nitrate, potassium nitrate, $N_2O_5$ and mixtures thereof. 22.

* * * * *